(12) United States Patent
Le

(10) Patent No.: US 10,406,011 B2
(45) Date of Patent: Sep. 10, 2019

(54) IMPLANTABLE MEDICAL DEVICE DELIVERY SYSTEM

(71) Applicant: Medtronic Vascular, Inc., Santa Rosa, CA (US)

(72) Inventor: Tony Le, Rohnert Park, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 533 days.

(21) Appl. No.: 15/140,881

(22) Filed: Apr. 28, 2016

(65) Prior Publication Data

US 2017/0312109 A1  Nov. 2, 2017

(51) Int. Cl.
*A61F 2/958* (2013.01)
*A61F 2/95* (2013.01)
*A61M 31/00* (2006.01)

(52) U.S. Cl.
CPC .......... *A61F 2/958* (2013.01); *A61F 2/95* (2013.01); *A61M 31/00* (2013.01); *A61F 2240/002* (2013.01)

(58) Field of Classification Search
CPC ...... A61F 2/95; A61F 2/958; A61F 2240/002; A61M 31/00
See application file for complete search history.

(56) References Cited

U.S. PATENT DOCUMENTS 5,409,495 A * 4/1995 Osborn ................ A61F 2/958
604/103.06
5,893,868 A * 4/1999 Hanson ................ A61F 2/0095
606/192
6,699,170 B1 * 3/2004 Crocker ............... A61N 5/1002
600/3
8,465,541 B2  6/2013 Dwork
8,568,474 B2  10/2013 Yeung et al.
8,945,145 B2  2/2015 Tran et al.
2003/0060832 A1  3/2003 Guinan et al.
(Continued)

FOREIGN PATENT DOCUMENTS

WO  99/27989 A1  6/1999
WO  2009/029674 A1  3/2009
WO  2010/077676 A1  7/2010

OTHER PUBLICATIONS

EP17168577.9, European Search Report, dated Oct. 20, 2017, 6pgs.

*Primary Examiner* — Julie A Szpira

(57) ABSTRACT

A system for delivering an implantable medical device to a treatment site within a patient includes an implantable medical device including a rigid body, and a delivery device. The delivery device includes an elongated catheter shaft and an expandable balloon connected to the elongated catheter shaft adjacent a distal end of the elongated catheter shaft, where the expandable balloon includes a proximal region, a distal region, and an implant retaining portion disposed between the proximal region and the distal region. The delivery device also includes a compression element connected to the implant retaining portion of the expandable balloon, where the compression element is adapted to limit expansion of the implant retaining portion of the expandable balloon when the expandable balloon is at least partially inflated. At least a portion of the compression element and the implant retaining portion are disposed within a lumen of the implantable medical device.

15 Claims, 6 Drawing Sheets

(56) References Cited

U.S. PATENT DOCUMENTS

| | | | |
|---|---|---|---|
| 2005/0055076 A1* | 3/2005 | Huxel | A61M 27/008 623/1.11 |
| 2006/0079957 A1* | 4/2006 | Chin | A61F 2/06 623/1.23 |
| 2006/0259117 A1* | 11/2006 | Pal | A61F 2/95 623/1.11 |
| 2011/0160575 A1* | 6/2011 | Beyar | A61M 25/104 600/424 |
| 2012/0035705 A1 | 2/2012 | Giasolli et al. | |
| 2014/0067049 A1 | 3/2014 | Costello | |
| 2014/0214155 A1 | 7/2014 | Kelley | |

\* cited by examiner

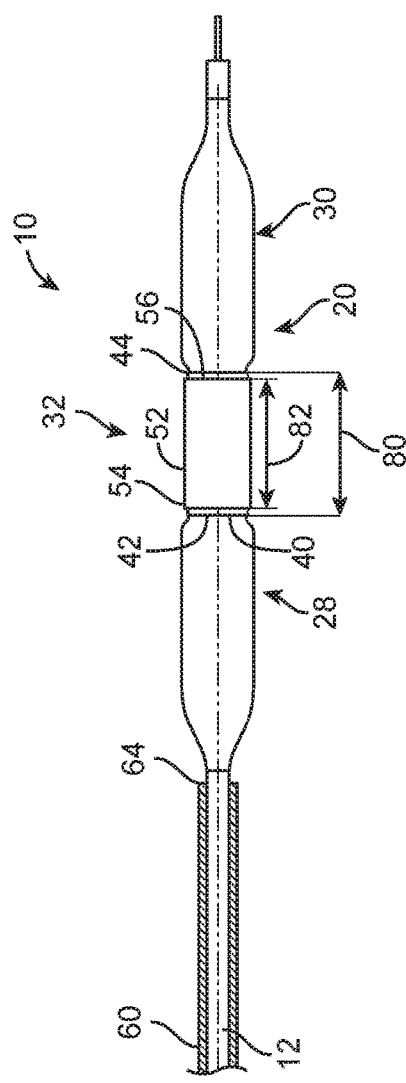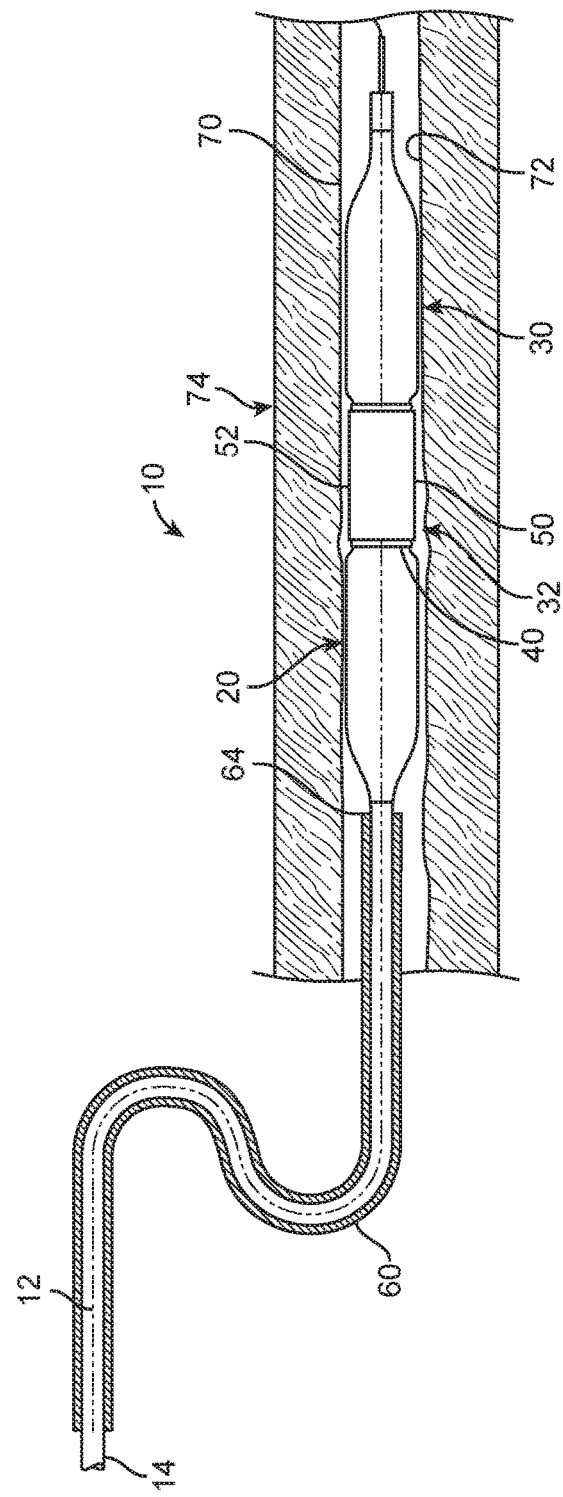

IMPLANTABLE MEDICAL DEVICE DELIVERY SYSTEM

FIELD

The present disclosure relates to, among other things, implantable medical devices; and more particularly to implantable medical device delivery systems.

BACKGROUND

Transluminal catheter deployment of an implantable medical device can provide an effective alternative to delivery of the implantable medical device to a treatment site within a patient using traditional surgical techniques. For example, a cardiac valve can be replaced with a prosthetic heart valve without requiring open-heart surgery by connecting the prosthetic heart valve to a collapsible and expandable support frame that can be loaded onto a delivery catheter. The prosthetic heart valve can then be advanced into a patient through the vasculature via the delivery catheter. In general, the prosthetic heart valve is loaded onto an expandable balloon of a delivery catheter by crimping or compressing a support frame of the valve onto the expandable balloon. The catheter and valve are then advanced, e.g., through an opening in the femoral artery and through the descending aorta to the heart where the valve is then deployed, e.g., in the aortic valve annulus. The prosthetic heart valve can be deployed by inflating the expandable balloon, thereby expanding the support frame of the valve until the valve engages tissue surrounding the treatment site. Alternatively, the support frame of the valve can be self-expanding. In this case, the support frame can be crimped down to a desired size without the use of an expandable balloon, and the frame can be held in a compressed arrangement within an outer delivery sheath. Retracting the sheath from the support frame enables the frame to self-expand to a larger diameter and engage tissue at the treatment site.

Many devices, such as the valves described above, are flexible and capable of withstanding expanding and compressing forces exerted by the delivery catheter, such as by a balloon expanding the valve or a sheath compressing the valve. However, some implantable devices include rigid bodies that may not be flexible enough to withstand the typical expanding and compressing forces exerted by a delivery catheter. For example, a drug or treatment material may be compressed into a rigid, pill-like form that would crack if acted upon by compressive forces. Thus, a delivery device and method for delivering such rigid body implants transluminally without breaking the rigid body would be beneficial.

SUMMARY

In general, the present disclosure provides various embodiments of a system for delivering an implantable medical device to a treatment site within a patient and a method of using such system. The system can include an implantable medical device and a delivery device. The delivery device can include an elongated catheter shaft, an expandable balloon connected to the elongated catheter shaft, and a compression element connected to an implant retaining portion of the expandable balloon. The compression element can be adapted to limit expansion of the implant retaining portion of the expandable balloon when the expandable balloon is at least partially inflated. In one or more embodiments, the implantable medical device can be connected to the delivery device such that at least a portion of the compression element and at least a portion of the implant retaining portion of the expandable balloon are disposed within a lumen defined by a rigid body of the implantable medical device.

In general, in one aspect, the present disclosure describes a system for delivering an implantable medical device to a treatment site within a patient. The system includes an implantable medical device including a rigid body, and a delivery device. The delivery device includes an elongated catheter shaft having a proximal end and a distal end, where the elongated catheter shaft defines a longitudinal axis extending between the proximal end and the distal end. The delivery device also includes an expandable balloon connected to the elongated catheter shaft adjacent the distal end of the elongated catheter shaft, where the expandable balloon includes a proximal region, a distal region, and an implant retaining portion disposed between the proximal region and the distal region. The delivery device also includes a compression element connected to the implant retaining portion of the expandable balloon, where the compression element is adapted to limit expansion of the implant retaining portion of the expandable balloon when the expandable balloon is at least partially inflated. The implantable medical device is connected to the delivery device such that at least a portion of the compression element and at least a portion of the implant retaining portion of the expandable balloon are disposed within a lumen defined by the rigid body of the implantable medical device.

In various embodiments, the compression element is adapted to prevent the expandable balloon from expanding within the lumen of the rigid body of the medical device. In certain embodiments, a longitudinal length of the compression element is equal to or greater than a longitudinal length of the rigid body of the implantable medical device such that the compression element extends along at least the entire lumen of the rigid body.

In various embodiments, the system also includes a sheath disposed over at least a portion of the elongated catheter shaft, where the sheath is adapted to engage the medical device and maintain the medical device in place as the expandable balloon and compression element are withdrawn through the lumen of the rigid body of the medical device. In certain embodiments, the sheath is further adapted such that the expandable balloon and compression element can be withdrawn through a lumen defined by the sheath.

In various embodiments, a diameter of the distal region of the expandable balloon adjacent a distal end of the implantable medical device is greater than an outer diameter of the distal end of the medical device when the expandable balloon is at least partially inflated.

In various embodiments, a diameter of the proximal region of the expandable balloon adjacent a proximal end of the implantable medical device is greater than an outer diameter of the proximal end of the medical device when the expandable balloon is at least partially inflated.

In various embodiments, the compression element includes tubing.

In various embodiments, the implantable medical device includes at least one of a hydroxyl-appetite calcium tube, a bone plug, a biostable tube, a bioabsorbable tube, a drug-coated shell, and a metal tube.

In various embodiments, a cross-sectional area of the distal region of the expandable balloon decreases in a distal direction along the longitudinal axis.

In various embodiments, the system also includes a therapeutic agent disposed on a surface of the expandable balloon.

In various embodiments, a maximum volume of the distal region of the expandable balloon is greater than a maximum volume of the proximal region of the expandable balloon.

In various embodiments, the expandable balloon is adapted to be deflated and withdrawn through the lumen of the rigid body of the implantable medical device, thereby leaving the medical device in place at the treatment site.

In various embodiments, the elongated catheter shaft further includes an inflation lumen disposed along the longitudinal axis that is in fluid communication with the expandable balloon.

In various embodiments, the elongated catheter shaft further comprises a guidewire lumen disposed along the longitudinal axis.

In general, in another aspect, the present disclosure describes a method of manufacturing a system for delivering an implantable medical device to a treatment site within a patient, where the implantable medical device includes a rigid body. The method includes connecting an expandable balloon to an elongated catheter shaft adjacent a distal end of the elongated catheter shaft, where the elongated catheter shaft extends along a longitudinal axis; and connecting a compression element to an implant retaining portion of the expandable balloon, where the expandable balloon further includes a proximal region and a distal region, and where the implant retaining portion is disposed between the proximal and distal regions. The method also includes positioning at least a portion of the compression element and the implant retaining portion of the expandable balloon within a lumen defined by the rigid body of the implantable medical device such that the medical device is disposed between the distal region and the proximal region of the expandable balloon; and inflating the expandable balloon such that a diameter of the distal region of the expandable balloon adjacent a distal end of the implantable medical device is greater than an outer diameter of the distal end of the medical device.

In various embodiments, inflating the expandable balloon further includes inflating the expandable balloon such that a diameter of the proximal region of the expandable balloon adjacent a proximal end of the implantable medical device is greater than an outer diameter of the proximal end of the medical device.

In general, in another aspect, the present disclosure describes a method of delivering an implantable medical device to a treatment site within a patient. The method includes connecting a compression element to an implant retaining portion of an expandable balloon, where the expandable balloon is connected to an elongated catheter shaft adjacent a distal end of the elongated catheter shaft, where the elongated catheter shaft extends along a longitudinal axis between the distal end and a proximal end, and where the expandable balloon further includes a proximal region and a distal region. The implant retaining portion is disposed between the proximal region and the distal region. The method further includes disposing an implantable medical device over the compression element and the implant retaining portion of the expandable balloon, where the medical device includes a rigid body; and inflating the expandable balloon such that a diameter of the distal region of the expandable balloon adjacent a distal end of the implantable medical device is greater than a diameter of the distal end of the implantable medical device. The method further includes advancing the expandable balloon into a vessel of the patient with the elongated catheter shaft such that the implantable medical device is disposed at the treatment site; deflating the expandable balloon; and withdrawing the expandable balloon and the compression element through a lumen defined by the rigid body of the medical device such that the medical device remains at the treatment site.

In various embodiments, inflating the expandable balloon further includes inflating the expandable balloon such that a diameter of the proximal region of the expandable balloon adjacent a proximal end of the implantable medical device is greater than an outer diameter of the proximal end of the medical device.

In various embodiments, the method also includes advancing a sheath over the elongated catheter shaft such that a distal end of the sheath engages the medical device prior to withdrawing the expandable balloon and the compression element through the lumen of the rigid body of the medical device to maintain the medical device at the treatment site.

The disclosure can be implemented to realize one or more of the following advantages. The compression element may prevent the expandable balloon from exerting expanding forces on the implantable medical device to the extent those expanding forces may break the implantable medical device. The compression element may be sized such that the implantable medical device freely moves over the compression element, longitudinally along the expandable balloon. Further, the compression element may shape the expandable balloon such that the proximal region and the distal region of the expandable balloon are wider than the implant retaining portion to prevent the implantable medical device from moving proximally or distally off the expandable balloon. Further still, the compression element may be sized such that the implantable medical device cannot move freely over the compression element by exerting a minimal expanding force on the implantable medical device, for example, as by an interference fit. These and other advantages and aspects of the present disclosure will be apparent from the detailed description below. In no event, however, should the above summaries or advantages be construed as limitations on the claimed subject matter, which subject matter is defined solely by the attached claims, as may be amended during prosecution.

All headings provided herein are for the convenience of the reader and should not be used to limit the meaning of any text that follows the heading, unless so specified.

The words "preferred" and "preferably" refer to embodiments of the disclosure that may afford certain benefits, under certain circumstances; however, other embodiments may also be preferred, under the same or other circumstances. Furthermore, the recitation of one or more preferred embodiments does not imply that other embodiments are not useful, and is not intended to exclude other embodiments from the scope of the disclosure.

The terms "distal" and "proximal" are used in the following description with respect to a position or direction relative to the treating clinician. "Distal" or "distally" is a position distant from or in a direction away from the clinician. "Proximal" and "proximally" is a position near or in a direction toward the clinician.

Further, the term "adjacent the distal end of the elongated catheter shaft" means that an element or component is disposed closer to the distal end of the elongated catheter shaft than to the proximal end of the shaft.

BRIEF DESCRIPTION OF THE DRAWINGS

Throughout the specification, reference is made to the appended drawings, where like reference numerals designate like elements, and wherein:

FIG. 2 is a schematic cross-section view of a portion of the system of FIG. 1.

FIG. 3 is a schematic cross-section view of the system of FIG. 1 disposed within a patient such that a medical device of the system is located at a treatment site.

DETAILED DESCRIPTION

Figure 1:
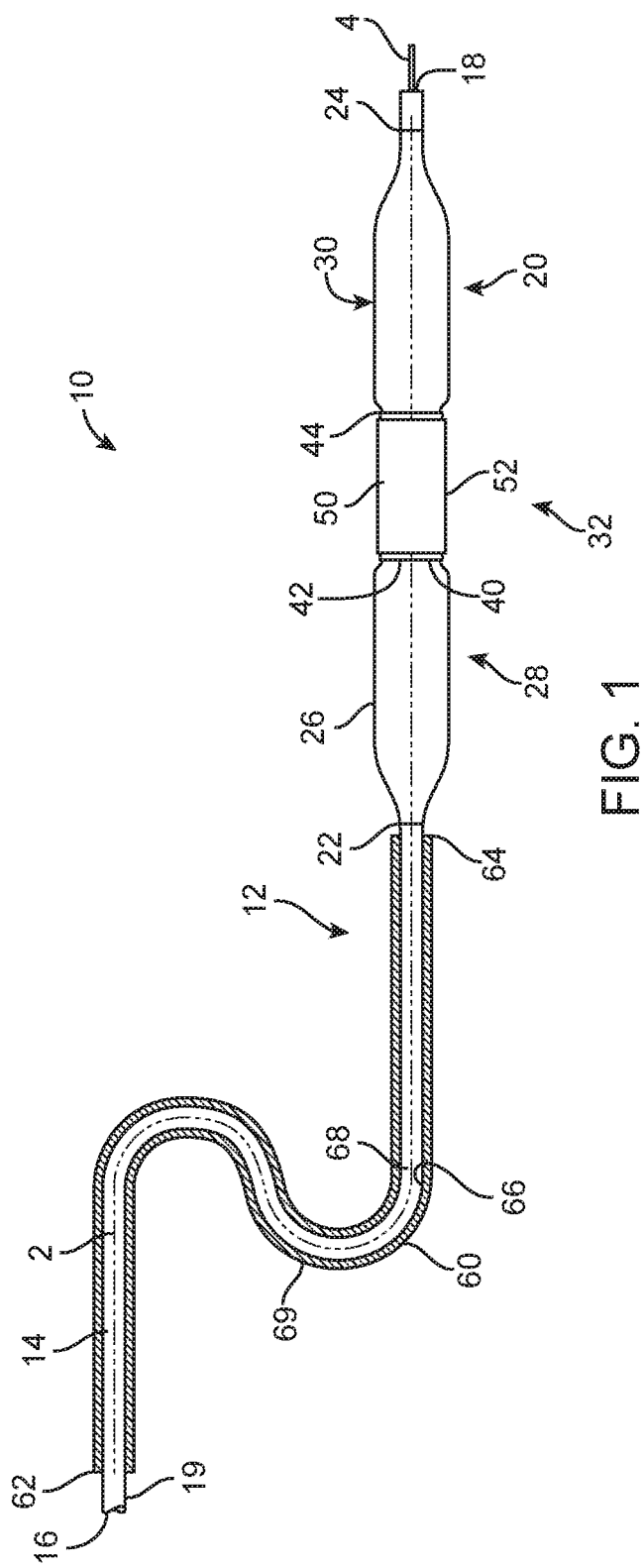
FIG. 1 is a schematic cross-section view of one embodiment of a system for delivering an implantable medical device.

In general, the present disclosure provides various embodiments of a system for delivering an implantable medical device to a treatment site within a patient and a method of using such system. The system can include an implantable medical device and a delivery device. The delivery device can include an elongated catheter shaft, an expandable balloon connected to the elongated catheter shaft, and a compression element connected to an implant retaining portion of the expandable balloon. The compression element can be adapted to limit expansion of the implant retaining portion of the expandable balloon when the expandable balloon is at least partially inflated. In one or more embodiments, the implantable medical device can be connected to the delivery device such that at least a portion of the compression element and at least a portion of the implant retaining portion of the expandable balloon are disposed within a lumen defined by a rigid body of the implantable medical device.

Balloon catheter delivery systems have been utilized to deliver implants such as valves, stents, and grafts. For example, a prosthetic heart valve can be delivered to a treatment site within a patient by crimping or compacting a support structure or frame of the valve onto an expandable balloon of a balloon catheter. The expandable balloon can be crimped in a middle portion by the implant, thereby limiting expansion of the expandable balloon while providing an interference fit between the expandable balloon and the implant, and distal and proximal regions of the expandable balloon can be at least partially inflated such that an outer diameter of one or both of these proximal and distal portions of the expandable balloon is at least the same as an outer diameter of an adjacent end of the implant. By at least partially inflating the expandable balloon such that the outer diameter is at least the same as or greater than the outer diameter of one or both ends of the implant, the expandable balloon can be at least flush with one or both ends of the implant and protect these ends as the implant is advanced into a vessel of a patient. The at least partially inflated expandable balloon can thus create a smooth junction between the outer surface of the expandable balloon and the ends of the implant to minimize any potential damage to inner walls of vessels caused by exposed edges of the implant as the balloon catheter is advanced along the vessel. Some implantable medical devices, however, include tubes or rigid bodies that cannot be crimped onto a balloon. In some cases, a rigid body of a medical device may be damaged by inflation of the expandable balloon within a lumen of the device. For example, the rigid body may be damaged by the expansion forces caused by the expandable balloon.

One or more embodiments of a system for delivering an implantable medical device to a treatment site within a patient described herein can deliver any suitable medical device to the treatment site, for example, devices that include a rigid body that cannot otherwise be crimped or compressed onto an expandable balloon of a balloon catheter, or that would be damaged by expansion forces of an expandable balloon. In one or more embodiments, the system can include a compression element that can be connected to an implant retaining portion of an expandable balloon of a balloon catheter. The compression element can be adapted to limit expansion of the implant retaining portion of the expandable balloon. An implantable medical device can be connected to the delivery device such that at least a portion of the compression element and at least a portion of the implant retaining portion of the expandable balloon are disposed within a lumen defined by the rigid body of the implantable medical device. In one or more embodiments, a distal region of the expandable balloon can be at least partially inflated such that an outer diameter of the distal region of the expandable balloon adjacent a distal end of the implantable medical device is equal to or greater than an outer diameter of the distal end of the implantable medical device. Further, in one or more embodiments, a proximal region of the expandable balloon can be at least partially inflated such that an outer diameter of the proximal region of the expandable balloon adjacent a proximal end of the implantable medical device is equal to or greater than an outer diameter of the proximal end of the implantable medical device.

One or both of the distal region and the proximal region of the expandable balloon when in this at least partially inflated configuration can provide a smooth transition from the expandable balloon to the rigid body of the implantable medical device such that ends of the implantable medical device are not exposed to the vessel as the implantable medical device is advanced into and along the vessel of the patient. By shielding or blocking the edges of the implantable medical device, an even surface of the expandable balloon and the rigid body of the implantable medical device can be created, thereby limiting surface damage to the vessel that could be caused by rough edges of the implantable medical device body. Further, at least partial inflation of one or both of the proximal region and the distal region of the expandable balloon can aid in retaining the implantable medical device in place over or on the implant retaining portion of the expandable balloon as the delivery device is advanced or withdrawn along the vessel. In one or more embodiments, upon delivery of the implantable medical device to the treatment site, the expandable balloon can be deflated, and the expandable balloon and the compression element can be withdrawn through the lumen of the rigid body of the implantable medical device, thereby deploying the implantable medical device at the treatment site.

In general, the various embodiments of systems described herein can be utilized to treat any suitable condition. For example, one or more embodiments of systems described herein can be utilized to treat, e.g., heart disease, various cardiovascular conditions, and other vascular conditions, including blockages, occlusions, stenoses or diseased regions in the coronary artery, femoral artery, peripheral arteries, and other arteries in the body. Exemplary treatments of vascular conditions can include the prevention or correction of various elements and deficiencies associated with the cardiovascular system, the cerebrovascular system, urine or genital system, biliary conduits, abdominal passageways, and other biological vessels within the body.

FIGS. 1-7 are various views of one embodiment of a system 10 for delivering an implantable medical device to a treatment site within a patient. The system 10 includes an implantable medical device 50 that includes a rigid body 52, and a delivery device 12 that includes an elongated catheter shaft 14 having a proximal end 16 and a distal end 18. The elongated catheter shaft 14 defines a longitudinal axis 2 that extends between the proximal end 16 and the distal end 18 of the elongated catheter shaft 14. The delivery device 12 also includes an expandable balloon 20 connected to the elongated catheter shaft 14 adjacent the distal end 18 of the elongated catheter shaft 14. The expandable balloon 20 includes a proximal region 28, a distal region 30, and an implant retaining portion 32 disposed between the proximal region 28 and the distal region 30.

Figure 6:
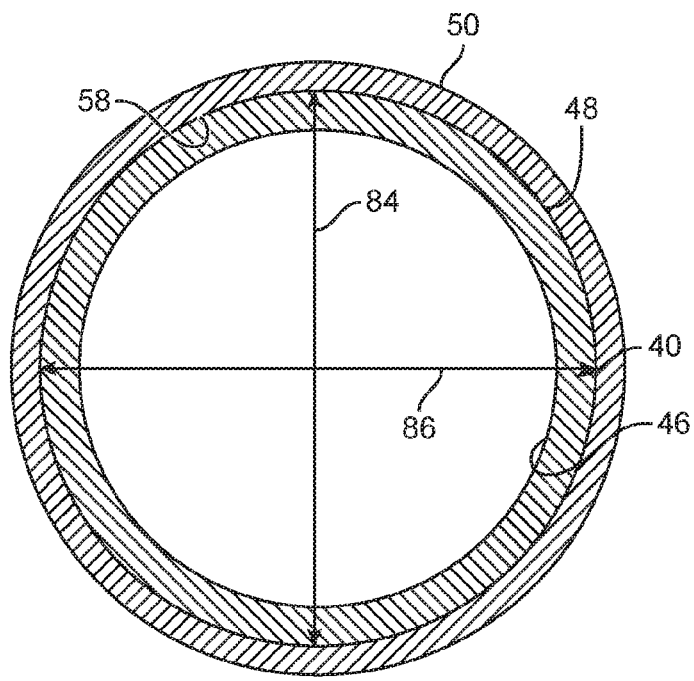
FIG. 6 is a schematic cross-section view of the implantable medical device, a compression element, and an implant retaining portion of an expandable balloon of the system of FIG. 1.

The delivery device 12 also includes a compression element 40 connected to the implant retaining portion 32 of the expandable balloon 20. The compression element 40 can be adapted to limit expansion of the implant retaining portion 32 of the expandable balloon 20 when the expandable balloon 20 is at least partially inflated. In one or more embodiments, the implantable medical device 50 is connected to the delivery device 12 such that at least a portion of the compression element 40 and at least a portion of the implant retaining portion 32 of the expandable balloon 20 are disposed within a lumen 58 (as shown in FIG. 6) defined by the rigid body 52 of the implantable medical device 50.

The implantable medical device 50 can include any suitable medical device that is designed to be implanted within a body of a patient. In one or more embodiments, the implantable medical device 50 can include a rigid body 52. As used herein, the term "rigid body" means a body of an implantable medical device that is not capable of being compressed or crimped onto the implant retaining portion 32 of the expandable balloon 20, or expanded by inflation of the expandable balloon 20. For example, an implantable medical device having a rigid body can include at least one of a hydroxyl-appetite calcium tube, a bone plug, a biostable tube, a bioabsorbable tube, a drug-coated shell, and a metal tube. The implantable medical device 50 also includes a proximal end 54, a distal end 56, and the lumen 58 (FIGS. 2 and 6) that is defined by the rigid body 52.

The implantable medical device 50 can include any suitable dimensions and take any suitable shape or combination of shapes. Further, the implantable medical device 50 can be a single, unitary piece or can include two or more pieces or elements that are connected together using any suitable technique or combination of techniques.

The implantable medical device 50 is connected to the delivery device 12. The delivery device 12 can include any suitable delivery device, e.g., a percutaneous transluminal angioplasty (PTA) balloon catheter. The elongated catheter shaft 14 of the delivery device 12 can include any suitable material or combination of materials and have any suitable dimensions. Further, the elongated catheter shaft 14 can take any suitable cross-sectional shape or combination of cross-sectional shapes. In one or more embodiments, the elongated catheter shaft 14 can include an inflation lumen (not shown) that is disposed along the longitudinal axis 2 and that is in fluid communication with the expandable balloon 20 such that the expandable balloon 20 can be inflated and deflated using any suitable technique or combination of techniques via the inflation lumen. Further, in one or more embodiments, the elongated catheter shaft 14 can also include a guidewire lumen (not shown) that is disposed along the longitudinal axis 2. The guidewire lumen of the elongated catheter shaft 14 can be adapted to guide the elongated catheter shaft 14 along a guidewire 4 that can be disposed within a patient such that the expandable balloon 20 can be guided to the treatment site within the patient.

The expandable balloon 20 is connected to the elongated catheter shaft 14 adjacent the distal end 18 of the elongate catheter shaft 14. In one or more embodiments, the expandable balloon 20 can include a proximal end 22, a distal end 24, and an exterior surface 26. The proximal end 22 and the distal end 24 of the expandable balloon 20 can be connected to the elongated catheter shaft 14 using any suitable technique or combination of techniques. In one or more embodiments, the proximal end 22 and the distal end 24 of the expandable balloon 20 can be connected to the elongated catheter shaft 14 such that an interior of the expandable balloon 20 is in fluid communication with an inflation lumen (not shown) disposed within the elongated catheter shaft 14. In such embodiments, the expandable balloon 20 can be inflated and deflated using, e.g., a pump or other inflation device connected to the inflation lumen of the elongated catheter shaft 14.

The expandable balloon 20 can include any suitable balloon or combination of balloons for use with balloon catheters. Further, the expandable balloon 20 can include any suitable dimensions and thicknesses. The expandable balloon 20 can include any suitable cross-sectional shape or combination of cross-sectional shapes in a plane that is transverse to the longitudinal axis 2, e.g., oval, rectangular, triangular, etc. The expandable balloon 20 can include a cross-sectional area that remains substantially the same along the longitudinal axis 2. In one or more embodiments, the expandable balloon 20 can include a cross-sectional shape that varies along the longitudinal axis, e.g., the expandable balloon includes a tapered portion or portions. While depicted as including a single balloon, the expandable balloon 20 can include two or more balloons that are connected together using any suitable technique or combination of techniques.

Expandable balloon 20 can be compliant, semi-compliant, or noncompliant. Semi-compliant and noncompliant balloons can be utilized for peripheral indications. The expandable balloon 20 can include any suitable material or combination of materials, metallic, polymeric, inorganic, etc. In one or more embodiments, the expandable balloon 20 can include a polymeric material, e.g., nylon, polyethylene terephthalate, polyethylene, high density polyethylene, polyamide copolymers, polyurethanes, polyvinylchloride, blends, copolymers, and multilayered combinations thereof.

The expandable balloon 20 includes the proximal region 28, the distal region 30, and the implant retaining portion 32 disposed between the proximal region 28 and the distal region 30. Each of the proximal region 28, the distal region 30, and the implant retaining portion 32 can have any suitable length as measured in a direction parallel to the longitudinal axis 2. The proximal region 28 and distal region 30 can have similar cross-sectional shapes or different cross-sectional shapes. Further, a volume of the proximal region 28 can be the same as or different from a volume of the distal region 30. In one or more embodiments, a maximum volume of the distal region 30 of the expandable balloon 20 can be greater than a maximum volume of the proximal region 28 of the expandable balloon. As used herein, the term "maximum volume" means the volume of a region or portion of the expandable balloon 20 when such region is inflated prior to failure of the expandable balloon 20. Further, the implant retaining portion 32 can have a maximum volume that is the same as or different from the maximum volume of one or both of the proximal region 28 and distal region 30.

Connected to the implant retaining portion 32 of the expandable balloon 20 is the compression element 40. In one or more embodiments, the compression element 40 can be adapted to limit expansion of the implant retaining portion 32 of the expandable balloon 20 when the expandable balloon 20 is at least partially inflated. In one or more embodiments, the compression element 40 is adapted to prevent expansion of the implant retaining portion 32 of the expandable balloon 20. Further, in one or more embodiments, the compression element 40 is adapted to prevent the expandable balloon 20 from expanding within the lumen 58 of the rigid body 52 of the implantable medical device 50.

The compression element 40 can include any suitable compression element or combination of elements, e.g., tubes or tubing, clamps, tapes, bands, etc. For example, for compression elements that include tubing, any suitable elastomeric material or combination of elastomeric materials may be utilized to form the tubing, e.g., polytetrafluoroethylene, polyamide, polyurethane, polyvinylchloride blends, copolymers, and multilayered combinations polymeric or metal tubing of various diameters and lengths depending on the design of the implant. Further, the compression element 40 can take any suitable shape or combination of shapes and have any suitable dimensions. For example, in one or more embodiments, the compression element 40 can have a longitudinal length 80 (as shown in FIG. 2) that can be equal to or greater than a longitudinal length 82 of the rigid body 52 of the implantable medical device 50 such that the compression element 40 extends along at least the entire lumen 58 of the rigid body 52. In one or more embodiments, the compression element 40 can take a circular cross-sectional shape in a plane transverse to the longitudinal axis 2. The compression element 40 can completely surround the implant retaining portion 32 of the expandable balloon 20. In one or more embodiments, the compression element 40 partially surrounds the implant retaining portion 32 of the expandable balloon 20.

Further, the compression element 40 can include an outer surface 48 (FIG. 6) that has any suitable diameter in relation to a diameter of the lumen 58 of the rigid body 52 of the implantable medical device 50. For example, FIG. 6 is a schematic cross-section view of the implant retaining portion 32 of the expandable balloon 20, the compression element 40, and the implantable medical device 50 taken in a plane transverse to the longitudinal axis 2 of the implant retaining portion 32 of the expandable balloon 20. As can be seen in FIG. 6, the outer surface 48 of the compression element 40 has an outer diameter 84. Further, the implantable medical device 50 includes a lumen 58 that has a diameter 86. In one or more embodiments, the diameter 86 of the lumen 58 of implantable medical device 50 is greater than the outer diameter 84 of the outer surface 48 of the compression element 40. In one or more embodiments, the diameter 86 of the lumen 58 is equal to the outer diameter 84 of the compression element 40 such that it is friction-fit with the outer surface 48 of the compression element 40. In still other embodiments, the compression element 40 may be made of a material that enables the compression element 40 to slightly expand within the lumen 58 of the rigid body 52. In such an embodiment, the outer diameter 84 of the compression element 40 may increase slightly, starting out at an outer diameter 84 slightly smaller than the diameter 86 of the lumen 58 of the rigid body 52 and increasing to a diameter 84 that is equal to the diameter 86 of the lumen 58 of the rigid body 52. In these embodiments, the compression element 40 may be configured to only enable slight expansion so as not to exert expansion forces, or large expansion forces, onto the rigid body 52.

Figure 7:
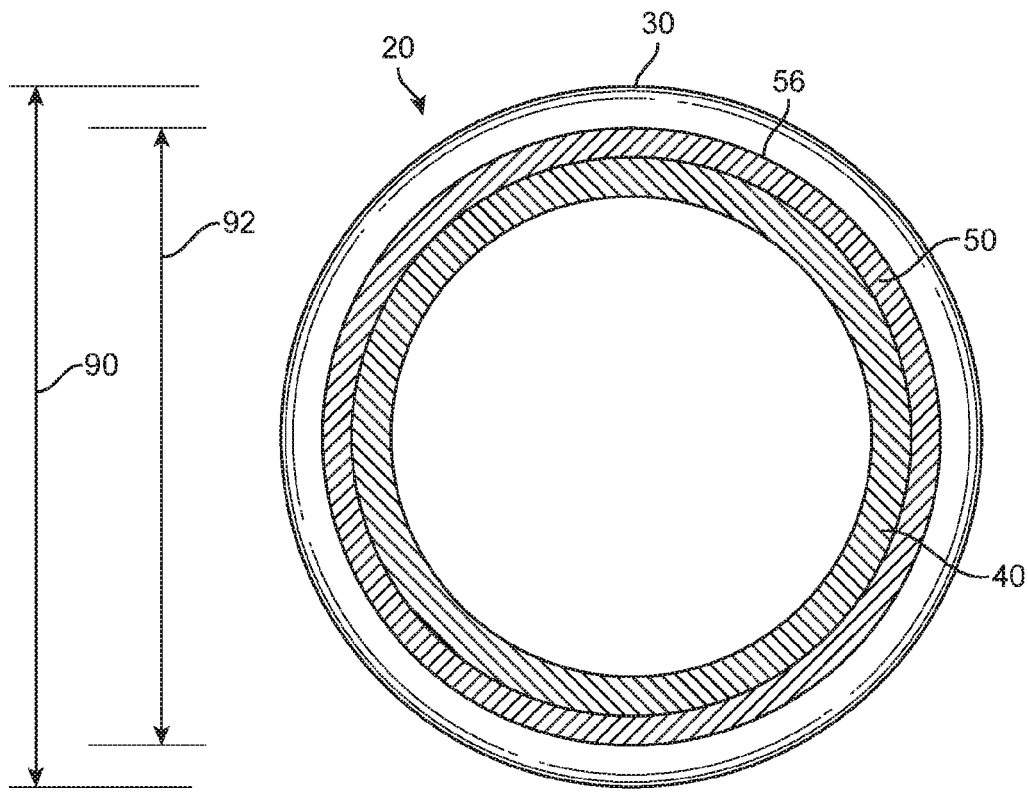
FIG. 7 is a schematic cross-section view of a distal region of the expandable balloon of the system of FIG. 1 as viewed in a proximal direction along a longitudinal axis.

In one or more embodiments, an outer diameter of one or both of the proximal region 28 and distal region 30 of the expandable balloon 20 can be selected such that the expandable balloon 20 can occlude one or both of the proximal end 54 and distal end 56 of the implantable medical device 50 when the expandable balloon 20 is at least partially inflated to minimize damage to an inner wall of a vessel that can be caused by the ends of the medical device as the delivery device 12 is advanced along the vessel or withdrawn from the vessel during a procedure. For example, FIG. 7 is a schematic cross-section view of the distal region 30 of the expandable balloon 20, the compression element 40, and the implantable medical device 50 taken in a plane transverse to the longitudinal axis 2 as viewed in a proximal direction along the longitudinal axis 2. The distal region 30 of the expandable balloon 20 includes an outer diameter 90 when the balloon is at least partially inflated. Further, the distal end 56 of the implantable medical device 50 includes an outer diameter 92. In one or more embodiments, the outer diameter 90 of the distal region 30 of the expandable balloon 20 adjacent the distal end 56 of the implantable medical device 50 (i.e., a portion of the distal region 30 of the expandable balloon 20 that is disposed closer to the implantable medical device 50 than to the distal end 24 of the expandable balloon 20) is equal to or greater than the outer diameter 92 of the distal end 56 of the implantable medical device 50 when the expandable balloon 20 is at least partially inflated. Although not shown, in one or more embodiments, an outer diameter of the proximal region 28 of the expandable balloon 20 adjacent the proximal end 54 of the implantable medical device 50 (i.e., a portion of the proximal region 28 of the expandable balloon 20 that is disposed closer to the implantable medical device 50 than to the proximal end 22 of the expandable balloon 20) is equal to or greater than an outer diameter of the proximal end 54 of the implantable medical device 50 when the expandable balloon 20 is at least partially inflated. In one or more embodiments, the outer diameter of each of the proximal region 28 and the distal region 30 of the expandable balloon 20 is greater than an outer diameter of each of the proximal end 54 and the distal ends 56 of the implantable medical device 50 when the expandable balloon 20 is at least partially inflated.

The system 10 can also include a sheath 60 disposed over at least a portion of the elongated catheter shaft 14. In one or more embodiments, the sheath 60 is adapted to engage the medical device 50 and maintain the medical device in place as the expandable balloon 20 and compression element 40 are withdrawn through the lumen 58 of the rigid body 52 of the medical device 50. Further, in one or more embodiments, the sheath 60 can also be adapted such that the expandable balloon 20 and compression element 40 can be withdrawn through a lumen 66 defined by the sheath.

The sheath 60 can include any suitable sheath or combination of sheaths. Further, the sheath 60 can be a single unitary sheath or a combination of two or more sheaths that are connected together using any suitable technique or combination of techniques. The sheath 60 includes a proximal end 62 and a distal end 64. The proximal end 62 of the sheath 60 can be disposed adjacent the proximal end 16 of the elongated catheter shaft 14. Further, the distal end 64 of the sheath 60 can be disposed adjacent the distal end 18 of the elongated catheter shaft 14. The sheath 60 also includes an inner surface 66 that defines the lumen 68.

The sheath 60 can have any suitable dimensions and take any suitable cross-sectional shape or combination of cross-sectional shapes. Further, the lumen 68 of the sheath 60 can have any suitable dimensions and take any suitable cross-sectional shape or combination of cross-sectional shapes. In one or more embodiments, a diameter of the lumen 68 of the sheath 60 can be selected such that the elongated catheter shaft 14 contacts the inner surface 66 of the sheath in one or more regions along the shaft to prevent fluid from entering the lumen 68 when at least a portion of the system 10 is disposed within the patient. In one or more embodiments, the elongated catheter shaft 14 includes an outer surface 19 that is friction-fit with the inner surface 66 of the sheath 60. In addition, an outer diameter 69 of the sheath 60 can have any suitable dimensions and take any suitable cross-sectional shape or combination of cross-sectional shapes. In one or more embodiments, the outer diameter 69 of the sheath is greater than the inner diameter 58 of the implantable medical device 50 to allow the distal end 64 of sheath 60 to engage with the proximal end 54 of the implantable medical device 50 to deploy the implantable medical device 50 as is further described herein.

At least a portion of the elongated catheter shaft 14 can be disposed within the lumen 68 of the sheath 60 using any suitable technique or combination of techniques. In one or more embodiments, the proximal end 16 of the elongated catheter shaft 14 can be inserted into the distal end 64 of the sheath 60, and the sheath 60 can be advanced over and along the elongated catheter shaft 14 in a distal direction. In one or more embodiments, the sheath 60 can include a slit that extends the length of the sheath 60 such that the elongated catheter shaft 14 can be inserted into the slit while the sheath 60 is advanced along the elongated catheter shaft 14 in a distal direction. In one or more embodiments, the sheath 60 can have a length along the longitudinal axis 2 that is less than, greater than, or equal to a length of the elongated catheter shaft 14.

The sheath 60 can include any suitable material or combination of materials, e.g., metallic, polymeric, inorganic, etc. In one or more embodiments, the sheath 60 can include an elastomeric material. Any suitable elastomeric material or combination of elastomeric materials may be utilized to form the sheath 60, e.g., polytetrafluoroethylene, polyamide, polyurethane, polyvinylchloride, blends, copolymers, and multilayered combinations thereof.

In one or more embodiments, one or more therapeutic agents can be disposed on at least one of the outer surface 26 of the expandable balloon 20 and the outer surface 69 of the sheath 60. Further, in one or more embodiments, a therapeutic agent can be disposed on or within the implantable medical device 50. Any suitable technique or combination of techniques can be utilized to dispose one or more therapeutic agents in any suitable location or portion of the system 10.

Any suitable therapeutic agent or combination of agents can be utilized with the system 10 depending upon the type of treatment that will be delivered to the treatment site within the patient. In general, a therapeutic agent is a composition that is capable of producing a beneficial effect against one or more conditions, including coronary restenosis, cardiovascular restenosis, angiographic restenosis, arterial sclerosis, hyperplasia, and other diseases or conditions. For example, a therapeutic agent can be selected to inhibit or prevent vascular restenosis, a condition corresponding to a narrowing or construction of the diameter of the bodily lumen where a stent can be placed. An anti-restenosis drug such as rapamycin, a rapamycin analog, or a rapamycin derivative may be used to prevent or reduce the recurrence of narrowing and blockage of the bodily vessel. In one or more embodiments, the antirestenosis drug paclitaxel can be utilized.

Figure 8:
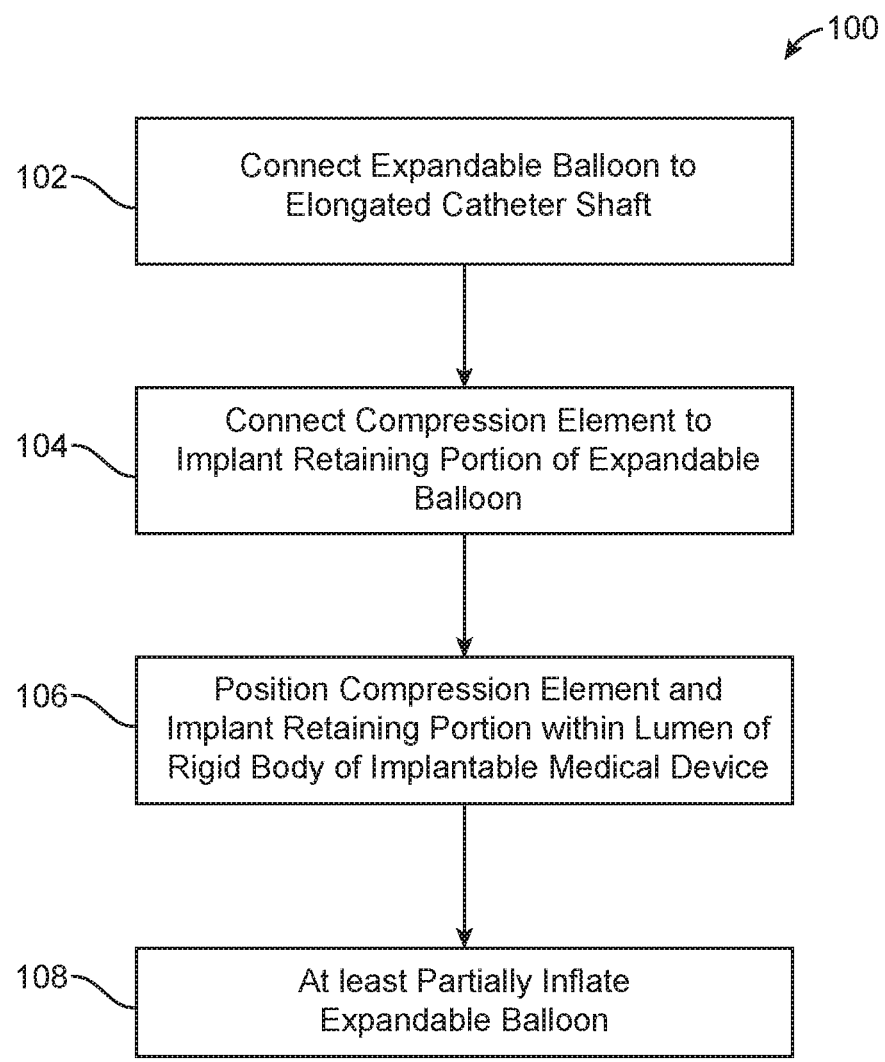
FIG. 8 is a flowchart of one method of forming the system of FIG. 1.

Any suitable technique or combination of techniques can be utilized to manufacture or assemble a system for delivering an implantable medical device to a treatment site within a patient. For example, FIG. 8 is a flowchart of one embodiment of a method 100 of manufacturing the system 10. Although described in regard to the system 10 of FIGS. 1-7 described herein, the method 100 can be utilized with any suitable system.

At 102, the expandable balloon 20 can be connected to the elongated catheter shaft 14 adjacent the distal end 18 of the elongated catheter shaft 14 using any suitable technique or combination of techniques. The compression element 40 can be connected to the implant retaining portion 32 of the expandable balloon 20 at 104 using any suitable technique or combination of techniques. For example, in one or more embodiments, the compression element 40 can be directed or slid over the outer surface 26 of the expandable balloon 20 until the compression element 40 is disposed over the implant retaining portion 32 of the expandable balloon. Further, in other embodiments, the compression element 40 can include a slit extending between the proximal end 42 and the distal end 44 of the compression element 40, and the expandable balloon 20 can be inserted through the slit such that the compression element 40 is connected to the implant retaining portion 32 of the expandable balloon 20.

At 106, at least a portion of the compression element 40 and the implant retaining portion 32 of the expandable balloon 20 can be positioned within the lumen 58 defined by the rigid body 52 of the implantable medical device 50 such that the implantable medical device 50 is disposed between the distal region 30 and the proximal region 28 of the expandable balloon 20. Any suitable technique or combination of techniques can be utilized to position at least a portion of the compression element 40 and the implant retaining portion 32 of the expandable balloon 20 within the lumen 58. In one or more embodiments, the compression element 40 and expandable balloon 20 can be directed or slid into the lumen 58 of the implantable medical device 50 by moving the implantable medical device 50 in a proximal direction over the distal region 30 of the expandable balloon 20 and the distal end 44 of the compression element 40.

The expandable balloon 20 can be at least partially inflated at 108. In some embodiments, the expandable balloon 20 can be at least partially inflated such that the diameter 90 of the distal region 30 of the expandable balloon adjacent the distal end 56 of the implantable medical device 50 is equal to or greater than the outer diameter 92 of the distal end 56 of the implantable medical device 50. Any suitable technique or combination of techniques can be utilized to inflate the expandable balloon 20. In one or more embodiments, the expandable balloon 50 can be inflated to any suitable volume such that the distal region 30 of the expandable balloon 50 shields the distal end 56 of the implantable medical device 50 as viewed in a proximal direction along the longitudinal axis 2. In one or more embodiments, the proximal region 28 of the expandable balloon 20 can be inflated such that the diameter of the proximal region 28 of the expandable balloon 20 adjacent the proximal end 54 of the implantable medical device 50 is equal to or greater than the outer diameter of the proximal end 54 of the medical device 50.

The manufacture or assembly of the system 10 can be done by any combination of entities. For example, in some embodiments, steps 102, 104, 106 and 108 may be carried out by a single entity and sold as a completed kit ready to use. In other embodiments, steps 102 and 104 may be carried out by one entity, for example, a manufacturer, and steps 106 and 108 may be carried out by another entity, for example, a treating physician. In the embodiments where a treating physician carries out steps 106 and 108, the ability to use different implantable medical devices is achieved. In other words, the delivery device 12 with the expandable balloon 20 and compression element 40 may be sold to a treating physician in one kit, and implantable medical devices 50 of varying types may be sold separately, so that the treating physician can decide which implantable medical device 50 is appropriate for the specific procedure and patient.

Figure 4:
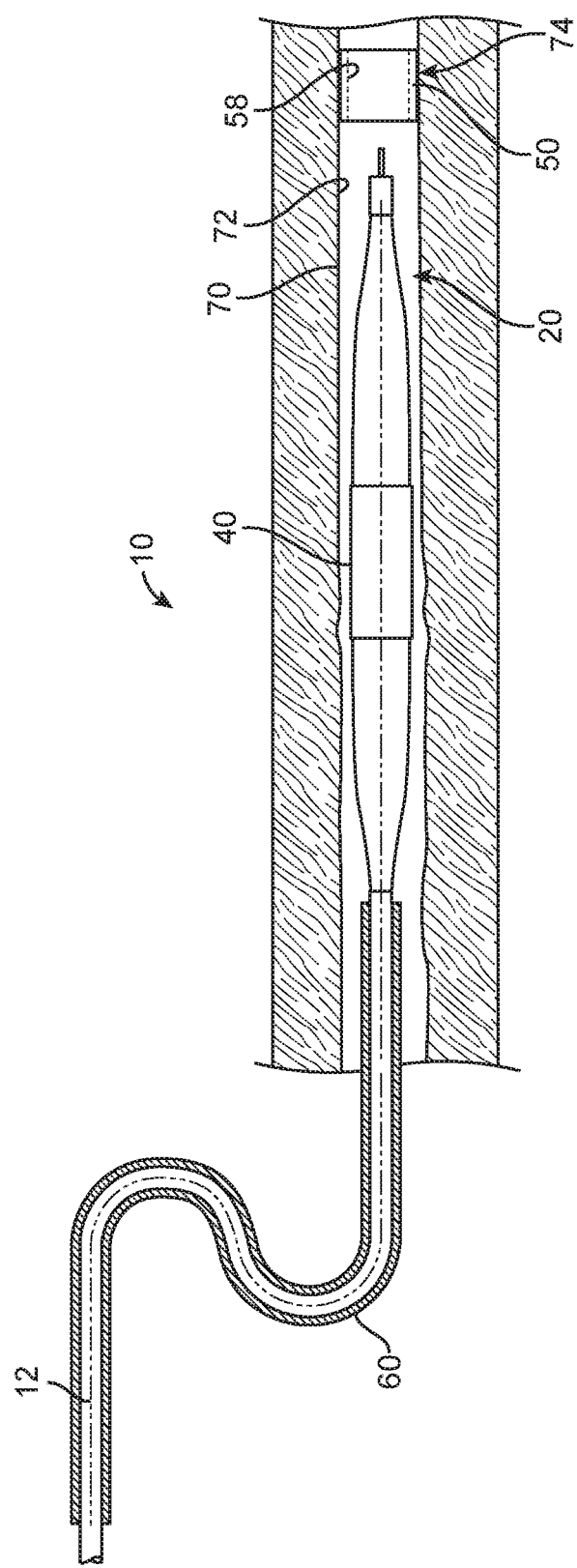
FIG. 4 is a schematic cross-section view of the system of FIG. 3 with the medical device having been deployed at the treatment site.
Figure 5:
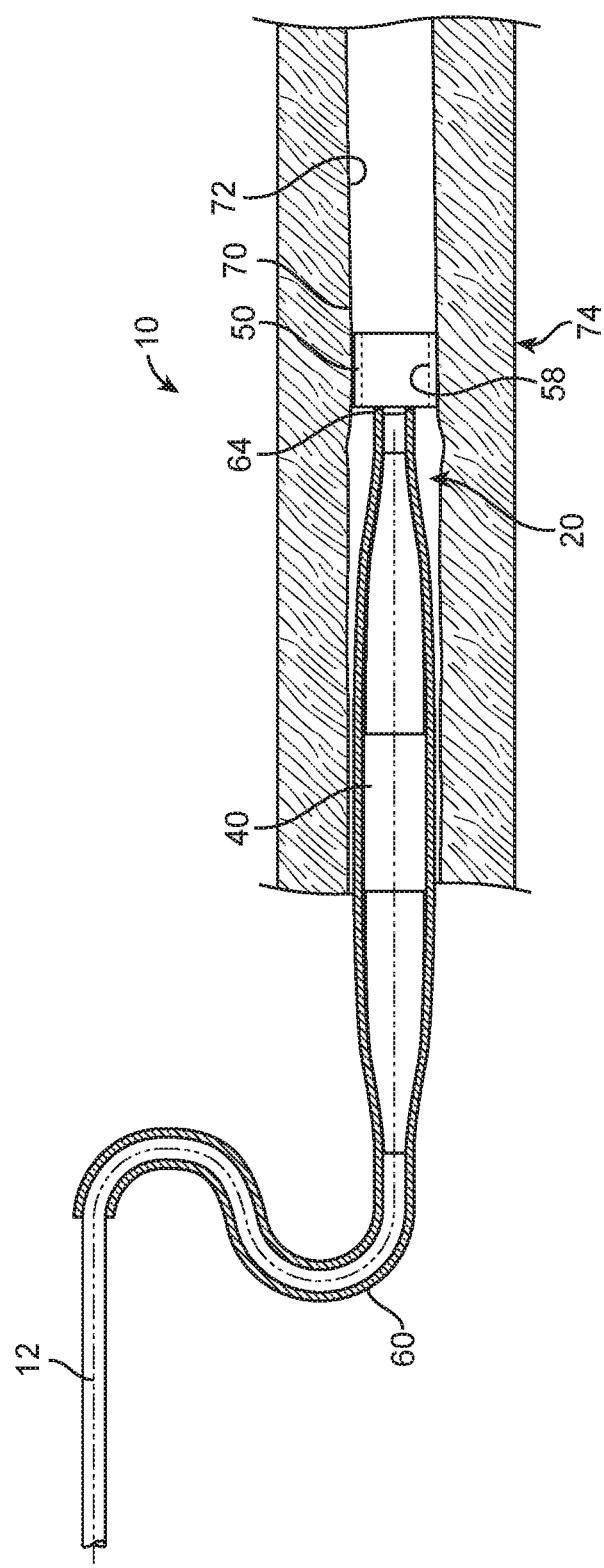
FIG. 5 is a schematic cross-section view of the system of FIG. 3 with a sheath of the system being utilized to assist in deploying the medical device at the treatment site.

Any suitable technique or combination of techniques may be utilized with the system 10 to deliver the implantable medical device 50 to the treatment site. For example, FIGS. 3-5 illustrate one embodiment of a method of delivering the implantable medical device 50 to a treatment site 74 disposed, e.g., on an inner surface 72 of a vessel 70. Although described in reference to the system 10 of FIGS. 1-2 and 6-7, any suitable system can be utilized with the method of FIGS. 3-5.

As shown in FIG. 3, the compression element 40 is connected to the implant retaining portion 32 of the expandable balloon 20 using any suitable technique or combination of techniques. The implantable medical device 50 can be disposed over the compression element 40 and the implant retaining portion 32 of the expandable balloon 20. The expandable balloon 20 can be inflated such that the diameter 90 of the distal region 30 of the expandable balloon 20 adjacent the distal end 56 of the implantable medical device 50 is equal to or greater than the outer diameter 92 of the distal end 56 of the implantable medical device 50. In one or more embodiments, the expandable balloon 20 can be inflated such that the diameter of the proximal region 28 of the expandable balloon adjacent the proximal end 54 of the implantable medical device 50 is equal to or greater than the outer diameter of the proximal end of the implantable medical device. The expandable balloon 20 can be advanced into a vessel 70 of the patient with the elongated catheter shaft 14 such that the implantable medical device 50 is disposed at a treatment site 74.

As shown in FIG. 4, the expandable balloon 20 can be deflated using any suitable technique or combination of techniques. Further, the expandable balloon 20 and the compression element 40 can be withdrawn through the lumen 58 of the implantable medical device 50 such that the implantable medical device 50 is deployed at the treatment site 74. In one or more embodiments, when the expandable balloon 20 is deflated, the inner wall 72 of the vessel 70 may contract to contact the implantable medical device 50 and retain the device at the treatment site 74.

In one or more embodiments, the sheath 60 of the system 10 may be adapted such that the distal end 64 of the sheath 60 can engage the implantable medical device 50 as shown in FIG. 5. As the distal end 64 of the sheath 60 engages the implantable medical device 50, the expandable balloon 20 and the compression element 40 can be withdrawn through the lumen 58 defined by the rigid body 52 of the implantable medical device 50 while the sheath 60 maintains the implantable medical device 50 at the treatment site 74. Once the expandable balloon 20 and the compression element 40 have been withdrawn from the lumen 58 of the implantable medical device 50, the sheath 60, the expandable balloon 20, and the compression element 40 can be withdrawn from the vessel while leaving the implantable medical device 50 deployed at the treatment site 74.

Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A system for delivering an implantable medical device to a treatment site within a patient, comprising:
   an implantable medical device comprising a rigid body;
   a delivery device comprising:
      an elongated catheter shaft comprising a proximal end and a distal end, wherein the elongated catheter shaft defines a longitudinal axis extending between the proximal end and the distal end;
      an expandable balloon connected to the elongated catheter shaft adjacent the distal end of the elongated catheter shaft, wherein the expandable balloon comprises a proximal region, a distal region, and an implant retaining portion disposed between the proximal region and the distal region; and
      a compression element connected to the implant retaining portion of the expandable balloon, wherein the compression element is adapted to limit expansion of the implant retaining portion of the expandable balloon when the expandable balloon is at least partially inflated;
   wherein the implantable medical device is connected to the delivery device such that at least a portion of the compression element and at least a portion of the implant retaining portion of the expandable balloon are disposed within a lumen defined by the rigid body of the implantable medical device, and further wherein the compression element is adapted to prevent the expandable balloon from expanding within the lumen of the rigid body of the implantable medical device.

2. The system of claim 1, wherein a longitudinal length of the compression element is equal to or greater than a longitudinal length of the rigid body of the implantable medical device such that the compression element extends along at least the entire lumen of the rigid body.

3. The system of claim 1, further comprising a sheath disposed over at least a portion of the elongated catheter shaft, wherein the sheath is adapted to engage the medical device and maintain the medical device in place as the expandable balloon and compression element are withdrawn through the lumen of the rigid body of the medical device.

4. The system of claim 3, wherein the sheath is further adapted such that the expandable balloon and compression element can be withdrawn through a lumen defined by the sheath.

5. The system of claim 1, wherein a diameter of the distal region of the expandable balloon adjacent a distal end of the implantable medical device is greater than an outer diameter of the distal end of the medical device when the expandable balloon is at least partially inflated.

6. The system of claim 1, wherein a diameter of the proximal region of the expandable balloon adjacent a proximal end of the implantable medical device is greater than an outer diameter of the proximal end of the medical device when the expandable balloon is at least partially inflated.

7. The system of claim 1, wherein the compression element comprises tubing.

8. The system of claim 1, wherein the implantable medical device comprises at least one of a hydroxyl-appetite calcium tube, a bone plug, a biostable tube, a bioabsorbable tube, a drug-coated shell, and a metal tube.

9. The system of claim 1, wherein a cross-sectional area of the distal region of the expandable balloon decreases in a distal direction along the longitudinal axis.

10. The system of claim 1, further comprising a therapeutic agent disposed on a surface of the expandable balloon.

11. The system of claim 1, wherein a maximum volume of the distal region of the expandable balloon is greater than a maximum volume of the proximal region of the expandable balloon.

12. The system of claim 1, wherein the expandable balloon is adapted to be deflated and withdrawn through the lumen of the rigid body of the implantable medical device, thereby leaving the medical device in place at the treatment site.

13. The system of claim 1, wherein the elongated catheter shaft further comprises an inflation lumen disposed along the longitudinal axis that is in fluid communication with the expandable balloon.

14. The system of claim 1, wherein the elongated catheter shaft further comprises a guidewire lumen disposed along the longitudinal axis.

15. A system for delivering an implantable medical device to a treatment site within a patient, comprising:
an implantable medical device comprising a rigid body;
a delivery device comprising:
an elongated catheter shaft comprising a proximal end and a distal end, wherein the elongated catheter shaft defines a longitudinal axis extending between the proximal end and the distal end;
an expandable balloon connected to the elongated catheter shaft adjacent the distal end of the elongated catheter shaft, wherein the expandable balloon comprises a proximal region, a distal region, and an implant retaining portion disposed between the proximal region and the distal region; and
a compression element connected to the implant retaining portion of the expandable balloon, wherein the compression element is adapted to limit expansion of the implant retaining portion of the expandable balloon when the expandable balloon is at least partially inflated;
wherein the implantable medical device is connected to the delivery device such that at least a portion of the compression element and at least a portion of the implant retaining portion of the expandable balloon are disposed within a lumen defined by the rigid body of the implantable medical device; and
wherein a diameter of the distal region of the expandable balloon adjacent a distal end of the implantable medical device is greater than an outer diameter of the distal end of the medical device when the expandable balloon is at least partially inflated.

* * * * *